United States Patent [19]

Purdy et al.

[11] Patent Number: 5,085,645
[45] Date of Patent: Feb. 4, 1992

[54] APPARATUS AND METHOD FOR A CATHETER ADAPTER WITH VALVE

[75] Inventors: Edmund R. Purdy, Fruit Heights; Mark A. Crawford, Sandy; Timothy J. Erskine; Gerald H. Peterson, both of Salt Lake City, all of Utah

[73] Assignee: Becton, Dickinson and Company, Franklin Lakes, N.J.

[21] Appl. No.: 569,797

[22] Filed: Aug. 15, 1990

[51] Int. Cl.⁵ .............................................. A61M 5/00
[52] U.S. Cl. ...................................... 604/167; 604/256
[58] Field of Search ................. 604/167, 256; 137/846; 251/149.1

[56] References Cited

U.S. PATENT DOCUMENTS

| | | | |
|---|---|---|---|
| 4,143,853 | 3/1979 | Abramson | 137/846 |
| 4,211,214 | 7/1980 | Chikashige | 604/256 |
| 4,424,833 | 1/1984 | Spector et al. | 604/167 |
| 4,874,377 | 10/1989 | Newgard et al. | 604/167 |
| 4,895,346 | 1/1990 | Steigerwald | 604/167 |
| 4,909,798 | 3/1990 | Fleischacker et al. | 604/256 |
| 4,917,668 | 4/1990 | Haindl | 604/167 |
| 4,960,412 | 10/1990 | Fink | 604/256 |
| 4,966,587 | 10/1990 | Baumgart | 604/167 |

Primary Examiner—Paul J. Hirsch
Attorney, Agent, or Firm—Aaron Passman; Arthur D. Dawson

[57] ABSTRACT

An over the needle catheter with adapter that has an integral valve in a passage. Distal and proximal parts form the adapter along an axis. The distal part communicates with a catheter. A hub conjugates with the proximal part and has a needle extending along the axis and through the passage when the hub is within the proximal part. A valve assembly has an elongate resilient member captured in the passage between the parts. A proximal portion of the valve assembly is engaged by a fitting to open the valve. A valve seat in the passage has a frusto-conical surface located coaxial about the axis and facing the distal part. The seat engages a chamfered surface on the elongate resilient member to seal and prevent flow and to allow flow when the seal is broken by axial compression of the elongate resilient member by the fitting. A septum like end across the elongate resilient member permits the needle to pass therethrough in a resealable fashion. The elongate resilient member has a diametrically reduced cylindrical body extending to the septum like end. The passage has an annular space about the reduced cylindrical body and terminates in a distal area. The distal area has flow channels which extend between the annular space and the distal part. A method has steps of locating the parts along an axis and capturing the elongate resilient member by engaging the axially aligned parts to force the elongate resilient member against a valve seat for sealing the passage and preventing flow. Placing a needle carried on a hub along the axis and through a septum like end of the elongate resilient member allows the needle to be withdrawn from the septum like end and to reseal the passage. Applying fastening means to secure the parts is a step.

11 Claims, 7 Drawing Sheets

APPARATUS AND METHOD FOR A CATHETER ADAPTER WITH VALVE

1. FIELD OF THE INVENTION

This invention relates to a bloodless over the needle catheter and more particularly, to a valve integral with a catheter adapter having a resealable septum through which the needle passes.

BACKGROUND

Over the needle catheters are used for peripheral intravenous entry into the vasculature of a patient. The disposable medical product is packaged as an assembly of a catheter adapter with its catheter and a needle and hub assembly conjugated with the catheter adapter such that the needle passes through the catheter tube and extends a slight distance beyond the distal tip thereof to provide a sharpened point for penetration through the skin of the human or animal being catheterized. During catheterization blood flows due to the vascular blood pressure through the hollow needle and into the transparent needle hub so it is visually apparent that the tip of the needle has reached into the blood vessel. Thereafter, the needle and hub as an assembly are removed from the catheter while the practitioner places a finger against the skin of the human or animal to compress the skin and the vessel therebeneath and distal to the catheter tube and thereby prevent the flow of blood through the catheter tube, into the catheter adapter and out onto the patient and the bedding. This approach has been used and is essentially bloodless, however, with greater concern about the spread of communicable diseases, particular those such as Acquired Immune Deficiency Virus and Hepatitis which are presently incurable, a need for a better technique, one that is automatically bloodless is required.

Use of an over the needle catheter is most conveniently performed by a single handed one finger technique. In particular, the needle and catheter assemblies are concentric and conjugate when they are inserted through the skin of the human or animal and into the vasculature. Once flashback is noted in the hub of the needle, a finger is generally placed on a portion of the catheter adapter and two other fingers of the same hand, one of which may be the thumb are used to control the hub. The finger on the catheter adapter pushes toward the patient such that the catheter and its adapter as an assembly are separated from the needle and hub assembly by the use of one hand. Practitioners usually use the other hand to hold the patient's arm steady, thus comforting the patient and enabling appropriate control of the procedure. It is of value to be able to withdraw the needle and hub assembly from the catheter and adapter assembly without having to use the hand which positions the patient's arm to also press against the catheter tube and stop blood flow. In that regard, a catheter adapter which includes an integral valve to automatically prevent blood loss would be of value in that the single handed technique described could be used without concern or need for the additional hand to prevent loss of blood from the catheter adapter.

Catheter adapters with manually actuated valves are shown in U.S. Pat. Nos. 3,811,440 and 3,856,010. Those manually actuated valves require that the valve in the catheter adapter be depressed during and after withdrawal of the needle and in that way the technique is similar to depressing the vessel but for the added expense of the valve. Valves actuated by the luer fitting on a syringe, administration set or the like are shown in U.S. Pat. Nos. 4,387,879 and 4,842,591. Those valves are normally closed and the insertion of the luer fitting into the housing containing the valve compresses the valve and opens a flow path.

U.S. Pat. No. 3,831,629 discloses a two piece check valve having a sleeve like valve body and valve element reciprocal therewithin. The valve element has an elastomeric rear end portion integral therewith and held in axial compression such that it is constantly urged forward toward a valve closed position. The proximal end of the valve element is crimped radially inward to form a fluid passing abutment and means is provided to guide the valve element for reciprocation within the body and maintain its concentric relative thereto. The mechanism is complicated in that a number of pieces are required to provide the integral valve and there is no showing of the valve in connection with an over the needle catheter assembly which permits a needle to pass through the valve.

U.S. Pat. No. 4,512,766 shows an assembly and needle hub with a needle passable through a penetratable self sealing material in the assembly. A slit or puncture is provided in the proximal end of the valve member which is spread upon axial compression by the luer of a syringe or the like. The slit provides a passage for the needle and also acts as the valve. Radial tension across the slit is relied on to close the valve member.

U.S. Pat. No. 4,874,377 shows a self occluding cannula assembly. The occluding means permits withdrawal of the needle and is in the form of an aperture which is either dialated by the tapered luer of a syringe or the like or penetrated by a needle passed therethrough. The aperture is formed by beveling the outward surface of the occluding member in each direction from the aperture such that a web of material closes the aperture. The aperture is torn by the radial spread of the forced luer and is eased by the thin material of the web. Resealing the aperture formed through the web is doubtful.

U.S. Pat. No. 3,385,301 shows a balloon catheter with a deformable one way inflation valve wherein a resilient valve member is captured in one leg of a Y adapter through which a syringe may be used to collapse the valve thus opening that path to air for inflating the balloon.

U.S. Pat. No. 4,681,132 has a check valve with a pre-set cracking pressure. The resilient member in this valve is biased by a plug which can be of varying heights adjusted to account for different tolerances of the valve bodies and the like. How the plug allows the manufacture with a pre set cracking pressure of this normally closed valve is the idea of this disclosure.

The aforesaid luer activated valves do not include in their designs sufficient capability for use with luers of varying dimensions. The engagement length of luer fittings can vary as much as 2.5 mm and still be considered to meet standard specifications. A positive seal upon withdrawal of the needle during the single handed introduction of an over the needle catheter assembly is required. These luer activated valves do not provide reliable activation of an automatic valve within the catheter adapter for the intravenous catheter. The catheter adapter with a valve as shown and disclosed in the present Specification overcomes the problems of the aforesaid valves.

SUMMARY OF THE INVENTION

An over the needle catheter and catheter adapter has an integral valve in a catheter adapter. The catheter adapter may have a distal part and a proximal part joined together to form a passage therethrough along an axis thereof. The distal part connects to a catheter tube providing fluid communication therewith and through the passage. A needle hub assembly has a hub which may conjugate with the proximal part of the catheter adapter and has a needle extending from the hub along the axis of the catheter adapter and through the passage when the hub is within the proximal part of the catheter adapter.

A valve assembly is most preferably positioned within the passage about the axis and has an elongate resilient member captured within the passage and between the distal part and the proximal part for a compression fit. The compression of the elongate resilient member prevents fluid communication through the passage. A proximal portion of the valve assembly is provided to be engaged by a fluid dispenser fitting such as a male luer connector fashioned to extend into the passage of the proximal part and contact the elongate resilient member. Axial compression of the elongate resilient member occurs when the fluid dispenser fitting is within the catheter adapter proximal part and opens the normally closed valve.

A valve seat disposed within the passage and on the proximal part is formed as a generally frusto conical surface located coaxial about the axis and facing the distal part of the catheter adapter in position to engage a chamfered surface on the elongate resilient member. The seat and the chamfered surface form a seal and prevent fluid communication when the elongate resilient member is compressed between the distal part and the proximal part but allow fluid communication when the seal is broken by axial compression of the elongate resilient member upon engagement of the fluid dispenser fitting with the proximal portion.

An internal cavity on the elongate resilient member extends axially and distally from the proximal portion providing a septum like end across the elongate resilient member for permitting the needle to pass through the septum like end of the elongate resilient member in a resealable fashion upon placement and withdrawal of the needle through the septum like end. The distal part and the proximal part each may be provided with conjugating surfaces arranged to fit together in mating engagement forming the passage through the catheter adapter. The elongate resilient member is preferably molded of a resilient material and has a flanged end for supporting the chamfered surface. The elongate resilient member has a diametrically reduced cylindrical body extending to the septum like end. An annular space formed about the diametrically reduced cylindrical body terminates in a distal area in the distal part.

The diametrically reduced cylindrical body and internal cavity therethrough act to provide an area of weakness permitting the elongate member to preferentially collapse under axial compression by the fluid dispenser fitting. A proximal end of the internal cavity of the elongate resilient member in the preferred embodiment conjugates with a collar disposed in axially alignment with the open end thereof and shaped to abut with the fluid dispenser fitting when extended into the distal part. The distal area may include flow channels which extend between the annular space and the distal part wherein the catheter tube joins in fluid communication the passage.

A method of providing a catheter adapter with an integral valve having an elongate resilient member which allows a needle to pass through the valve in a resealable manner includes the catheter adapter having a distal part and a proximal part which are designed to fit together and capture the elongate resilient member. The method has the steps of locating either of the parts along an axis for placing the elongate resilient member along the axis of the aligned part. Thereafter the step of placing the remaining part along the axis and moving it along the axis toward the other part captures the resilient member in a passage defined by the assembly of the parts.

Engaging the axially aligned parts with each other and about the elongate resilient member to axially compress the elongate resilient member in the passage in which the resilient member is captured is the next step. Forcing the elongate resilient member against a valve seat to seal transversely the passage and prevent flow therethrough is the valve forming step of the preferred method. Placing a needle carried on a hub along the axis and through a septum like end of the elongate resilient member allows the needle to be withdrawn from the septum like end to thereafter reseal the passage.

The method step of engaging is provided by fitting the parts and applying fastening means to secure in fluid tight manner the engagement between the parts. It is preferred that the elongate resilient member be placed into the distal part first before the proximal part is applied to complete the catheter adapter and compress the elongate resilient member within the passage formed therethrough.

DETAILED DESCRIPTION OF THE DRAWINGS

While this invention is satisfied by embodiments in many different forms, there is shown in the drawings and will herein be described in detail, a preferred embodiment of the invention and an alternate, with the understanding that the present disclosure is to be considered as exemplary of the principles of the invention and is not intended to limit the invention to the embodiment illustrated. The scope of the invention will be measured by the appended claims and their equivalents.

Figure 1:
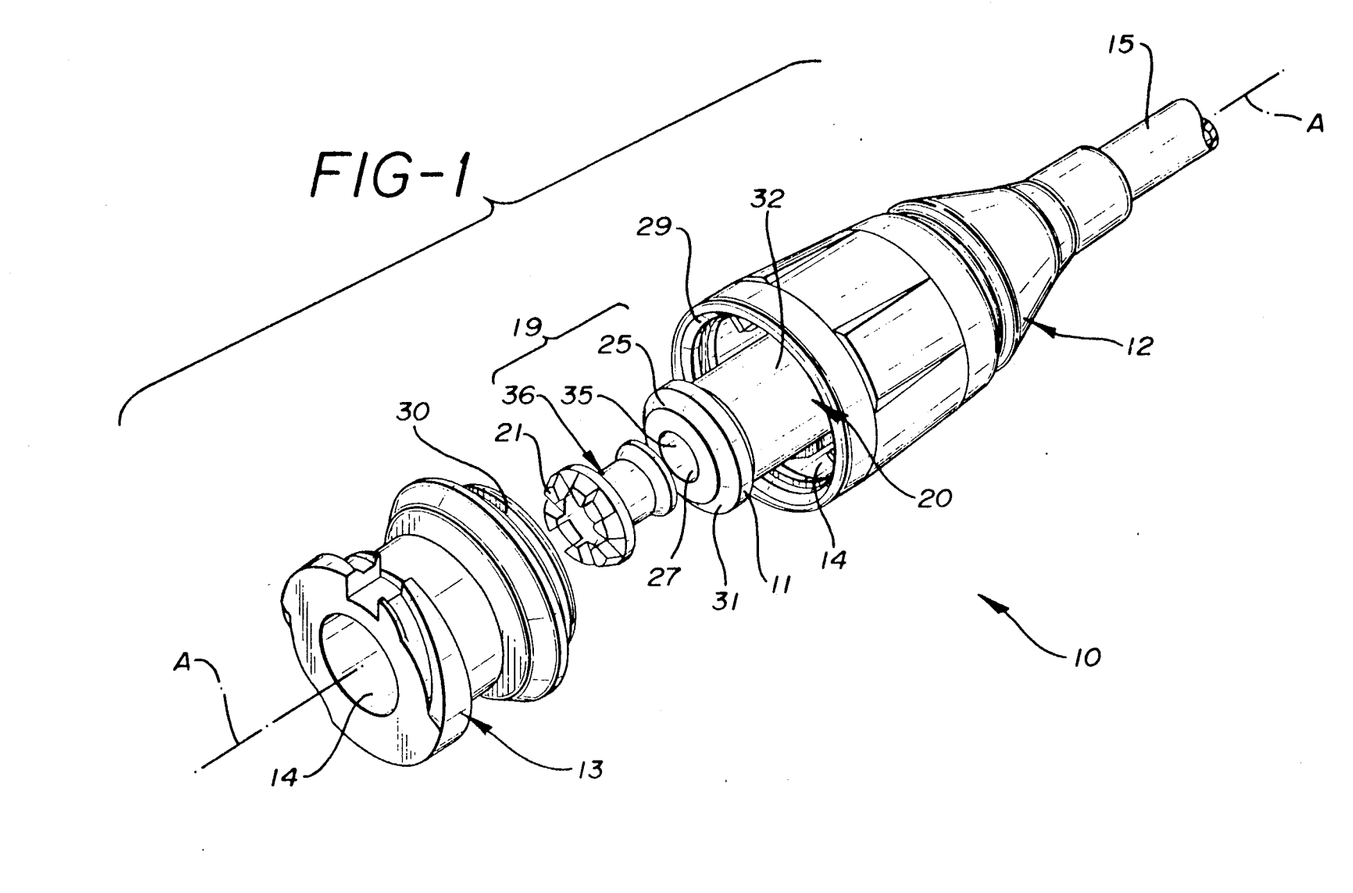
FIG. 1 discloses an exploded perspective view of a preferred embodiment of a catheter adapter with an integral valve.
Figure 3:
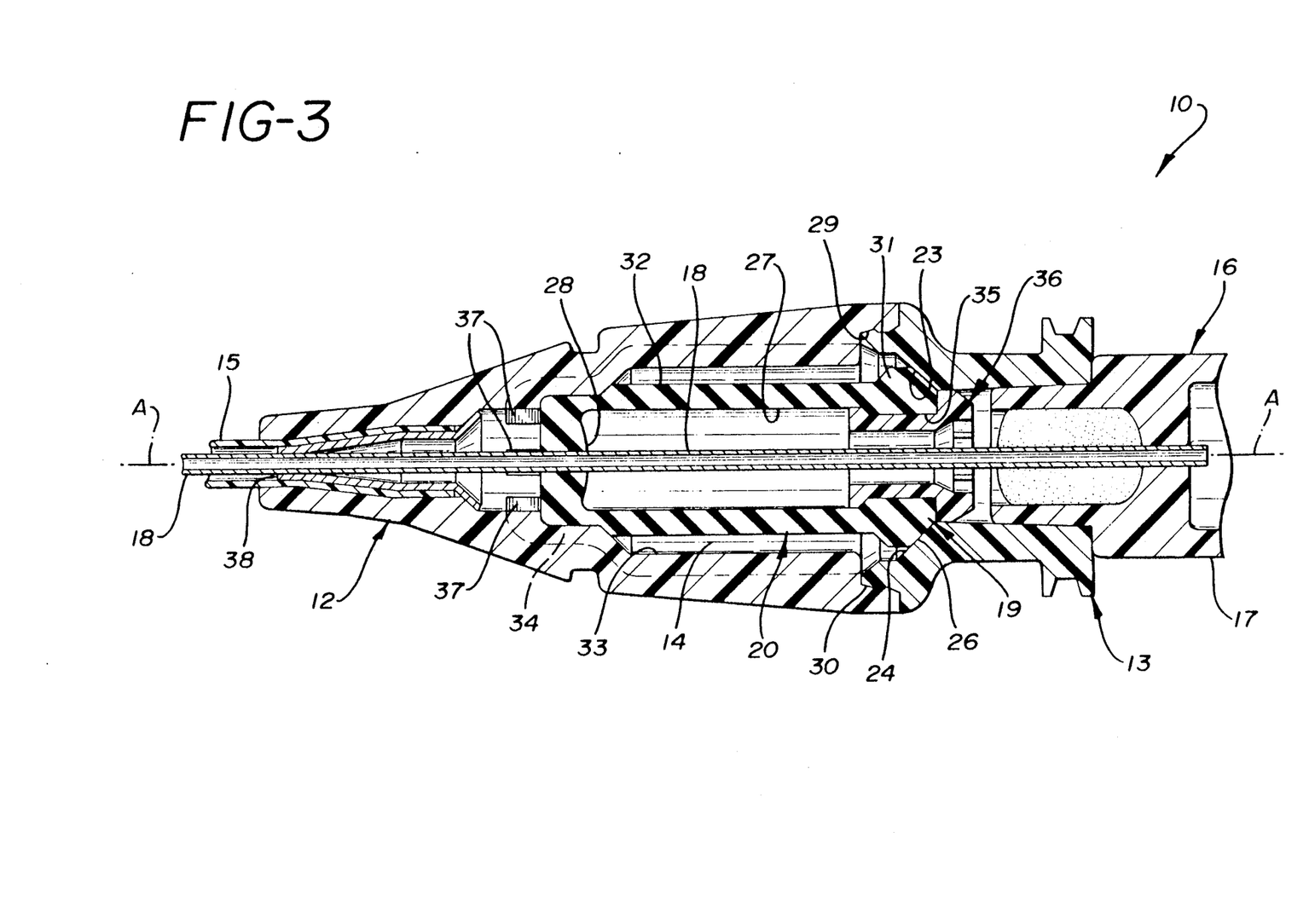
FIG. 3 is a cross-sectional view similar to FIG. 2 with the needle and hub assembly shown inserted through an elongate resilient member of the valve.

FIG. 1 is an exploded perspective view of the preferred embodiment of catheter adapter 10 An integral valve 11 is in a catheter adapter 10. The catheter adapter 10 may have a molded plastic distal part 12 and a molded plastic proximal part 13 joined together to form a passage 14 therethrough along an axis "A" thereof. The preferred plastic is polypropylene but polycarbonate, acrylic and PVC are also satisfactory substitutes. The distal part 12 connects to a catheter tube 15 providing fluid communication therewith and through the passage 14. In FIG. 3 a needle hub assembly 16 has a hub 17 which may conjugate with the proximal part 13 of the catheter adapter 10 and has a needle 18 extending from the hub 17 along the axis "A" of the catheter adapter 10 and through the passage 14 when the hub 17 is within the proximal part 13 of the catheter adapter 10.

Figure 4:
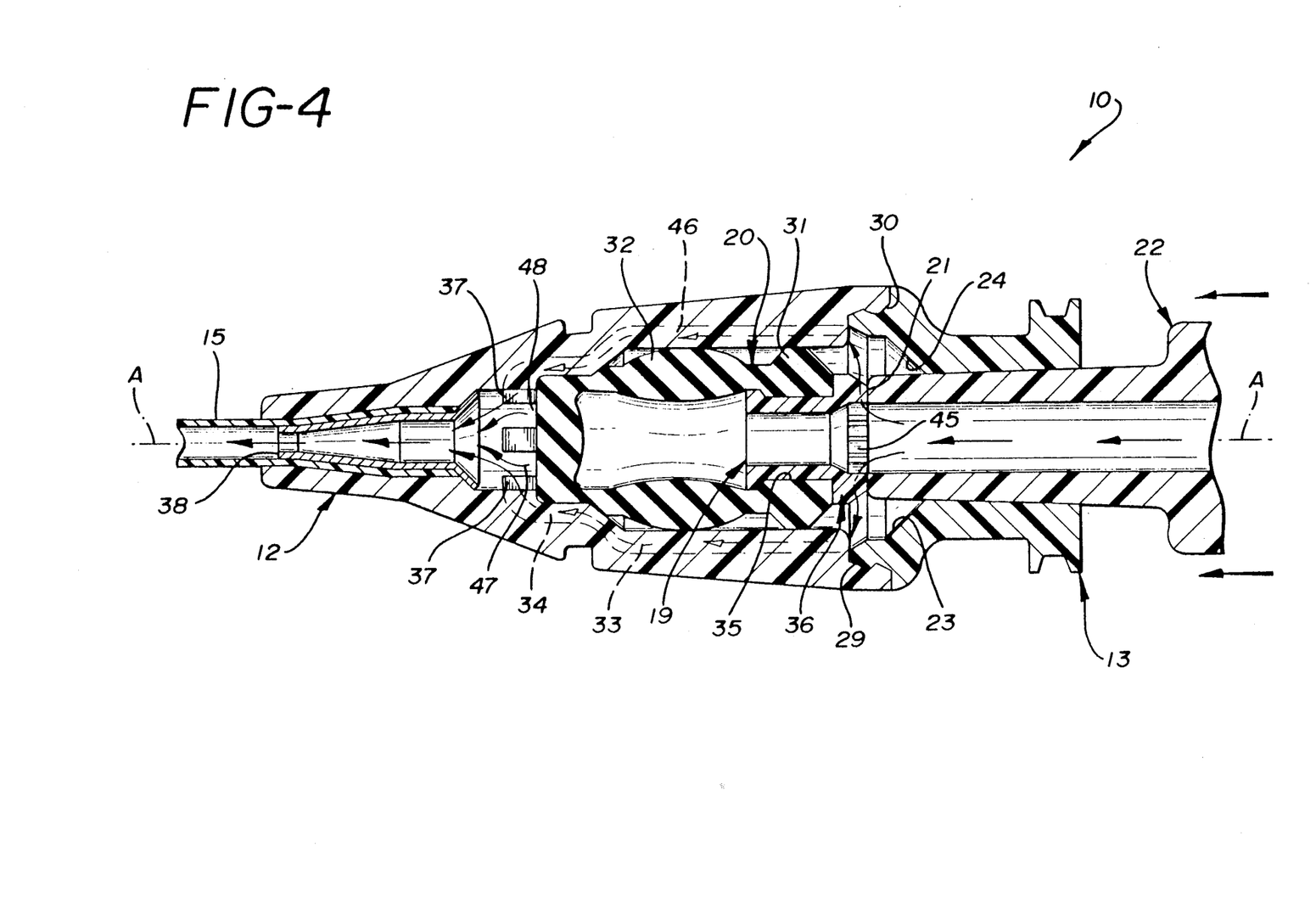
FIG. 4 is a cross sectional view similar to FIG. 2 with the needle and hub assembly removed and a luer fitting inserted to compress the elongate resilient member of the normally closed valve.
Figure 5:
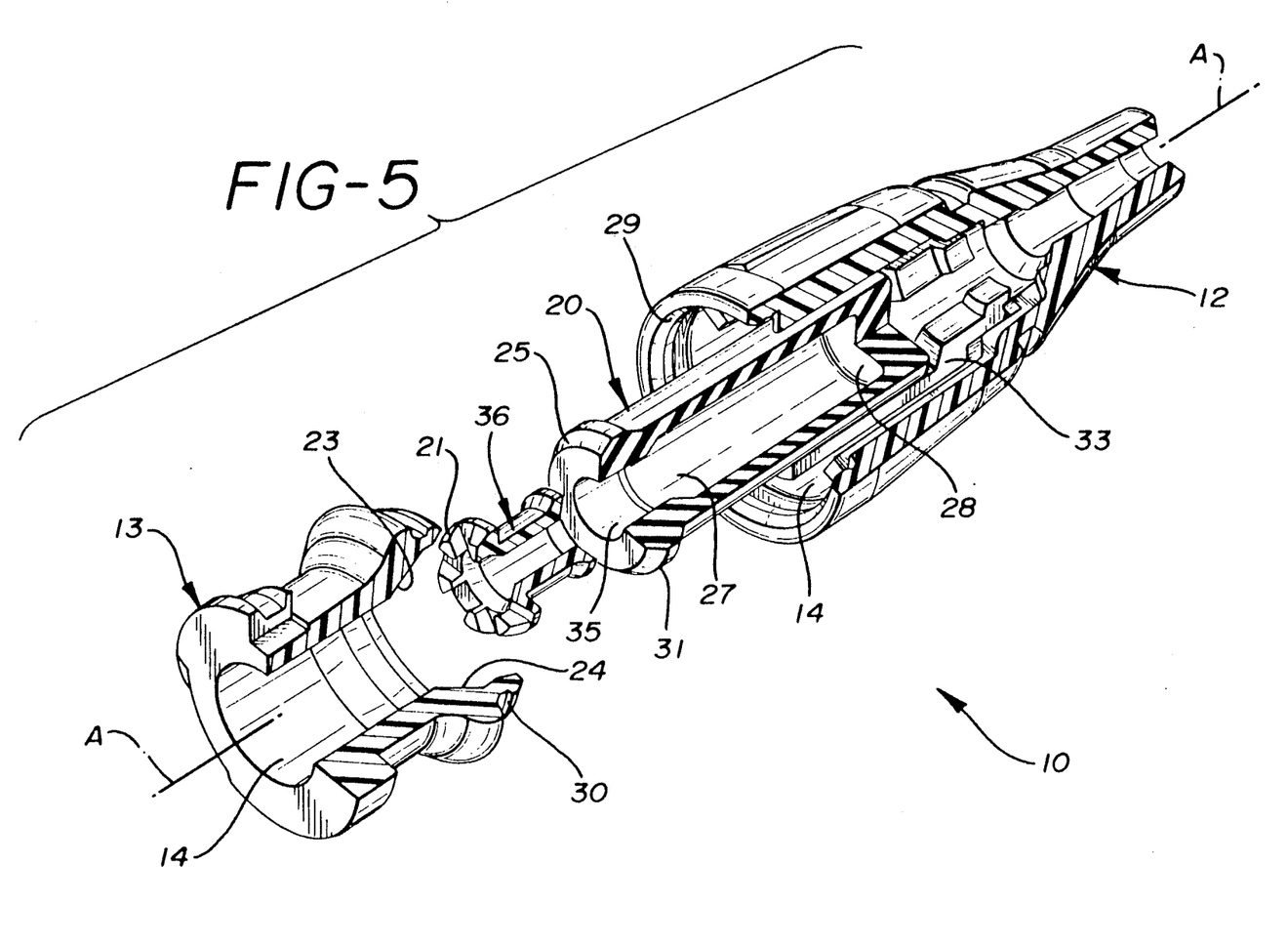
FIG. 5 discloses an exploded perspective view of the preferred embodiment of a catheter adapter with an integral valve of FIG. 1 with a section of the adapter removed so that the relationship of the parts may be shown.

A valve assembly 19 is most preferably positioned within the passage 14 about the axis "A" and has an elongate resilient member 20 captured within the passage 14 and between the distal part 12 and the proximal part 13 for a compression fit. The elongate resilient member 20 is most preferably molded of a flexible material such as rubber, urethane, latex, synthetic polymers or other elastomers. The preferred durometer of the elongate resilient member 20 is 40 to 50 Shore A. The compression of the elongate resilient member 20 prevents fluid communication through the passage 14, as will be explained. A proximal portion 21 of the valve assembly 19 is provided to be engaged by a fluid dispenser fitting 22 fashioned to extend into the passage 14 of the proximal part 13 and contact the elongate resilient member 20. As shown in Figure 4, the axial compression of the elongate resilient member 20 occurs when the fluid dispenser fitting 22 is within the proximal part 13 and opens the normally closed valve assembly 19.

Figure 2:
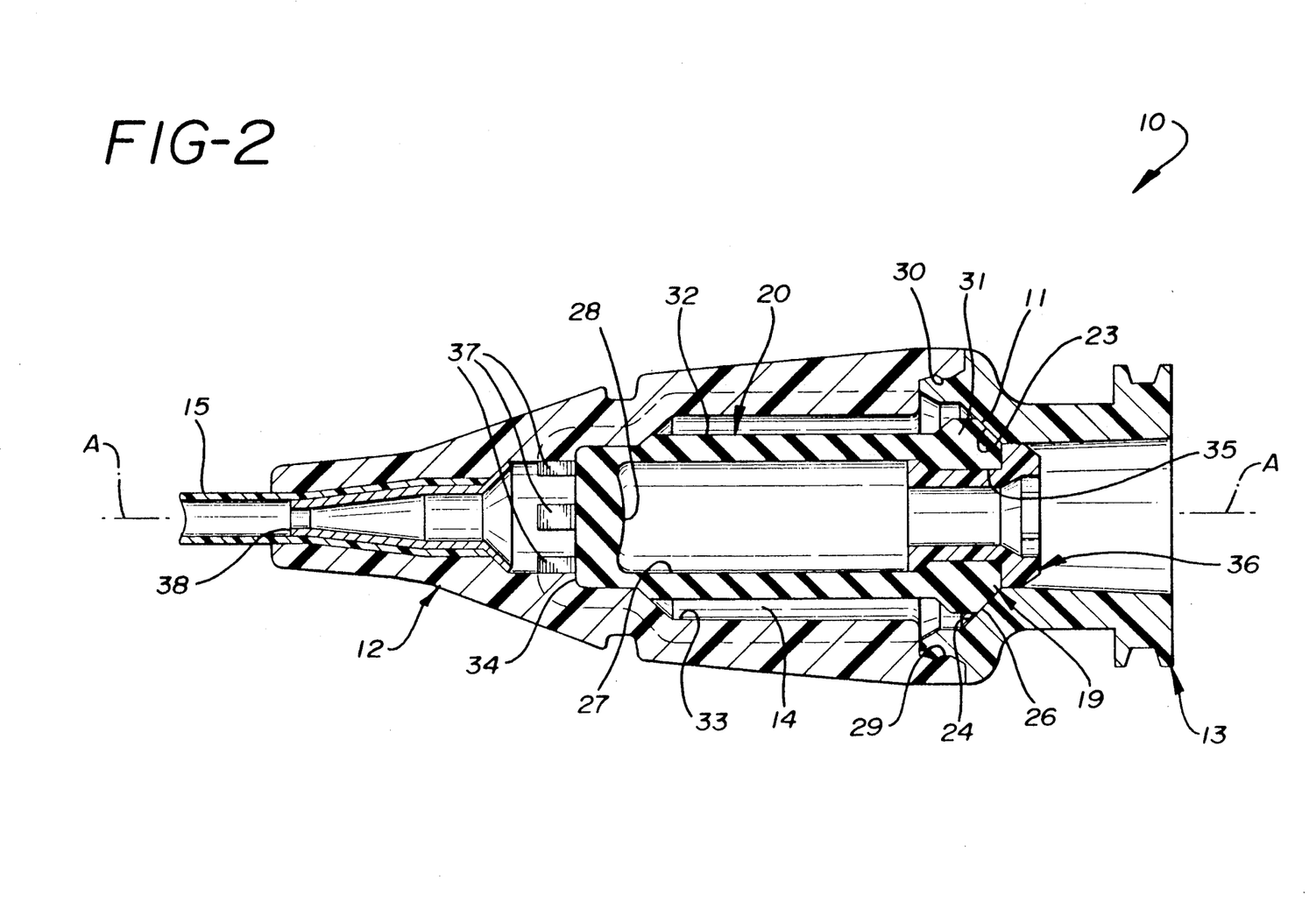
FIG. 2 discloses side cross sectional view of the valve shown in FIG. 1 except the valve is fully assembled with the parts shown in the positions they would be in before insertion of the needle and hub assembly therethrough.

A valve seat 23 as seen in FIGS. 2, 3 and 4 is disposed within the passage 14 and is on the inside of proximal 13 part. The valve seat 23 is formed as a generally frusto conical surface 24 located coaxial about the axis "A" and facing the distal part 12 of the catheter adapter 10 in position to engage a chamfered surface 25 on the elongate resilient member 20 as best seen. The valve seat 24 and the chamfered surface 25 form a seal 26 and prevent fluid communication when the elongate resilient member 20 in Figure 2 is compressed between the distal part 12 and the proximal part 13 but allow fluid communication when the seal 26 is broken by axial compression of the elongate resilient member upon engagement of the fluid dispenser fitting 22 within the proximal portion 13. The closed and open positions of the valve assembly 19 are shown in Figures 2 and 4.

An internal cavity 27 on the elongate resilient member 20 extends along axis "A" and distally from the chamfered surface providing a septum like end 28 across the elongate resilient member 20 for permitting the needle 18 to pass through the septum like end 28 of the elongate resilient member 20 in a resealable fashion upon placement and withdrawal of the needle through the septum like end 28. FIG. 3 shows the needle 18 passing through the septum like end 28 of the elongate resilient member 20. The distal part 12 and the proximal part 13 each may be provided with conjugating surfaces 29 and 30 respectively arranged to fit together in mating engagement forming the passage 14 through the catheter adapter 10. The elongate resilient member 20 as mentioned is preferably molded of a resilient material and has a flanged end 31 for supporting the chamfered surface 25. The elongate resilient member 20 has a diametrically reduced cylindrical body 32 extending to the septum like end 28. An annular space 33 formed about the diametrically reduced cylindrical body 32 terminates in a distal area 34 in the distal part 12.

The diametrically reduced cylindrical body 32 and internal cavity 27 therethrough act to provide weakness permitting the elongate resilient member 20 to preferentially collapse under axial compression by the fluid dispenser fitting 22. A proximal end 35 of the internal cavity 27 of the elongate resilient member in the preferred embodiment conjugates with a collar 36 disposed in axially alignment with the opening thereof. The collar 36 is shaped to abut with the fluid dispenser fitting 22 when it is extended into the distal part 12. The distal area 34 may include flow channels 37 which extend between the annular space 33 and the distal part 12 wherein the catheter tube 15 joins in fluid communication the passage 14, see FIGS. 2, 3, 4 and 6. The catheter 15 is held in the distal part 12 by an eyelet 38 preferably formed of metal; the eyelet 38 fits inside the catheter 15 and expands it against the inside of the distal part 12.

Figure 6:
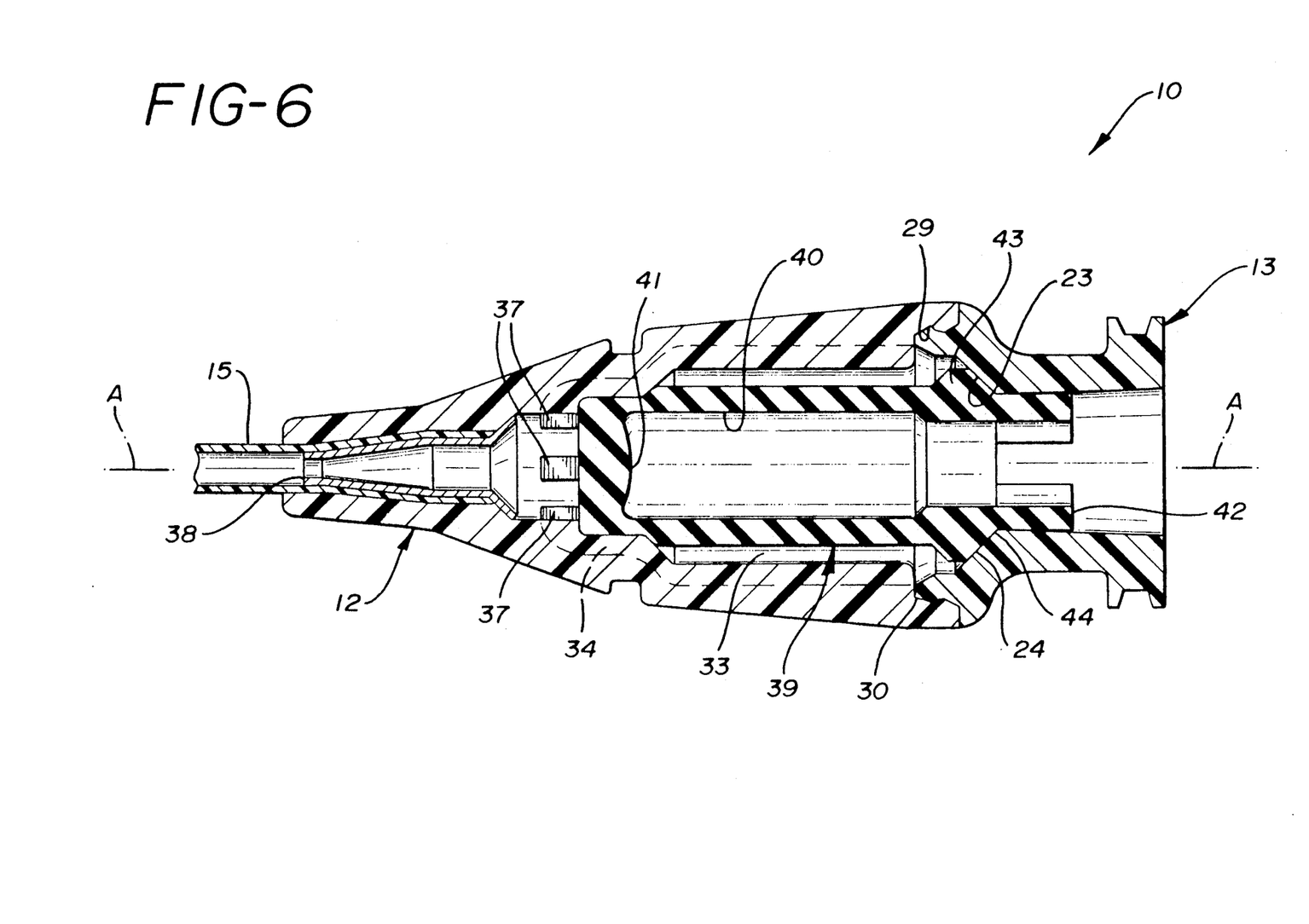
FIG. 6 discloses a side cross sectional view of an alternate valve with the parts shown in the positions they would be in before insertion of the needle and hub assembly therethrough.

FIG. 6 shows the alternate embodiment and all of the component parts therein are identical to those shown and described in connection with Figures 1, 2, 3, 4 and 5 except for the elongate resilient member 20 and collar 36. In FIG. 6 a single molded flexible piece 39 is substituted for the resilient member 20 and collar 36. In particular, single piece 39 has a hollow cylinder 40 terminating distally in a pierceable diaphragm 41. The hollow cylinder 40 has a partially split and longitudinally open annular extension 42 about its proximal end so that flow may pass through the proximal part when the piece 39 is axially compressed. Between the partially split and longitudinally open annual extension 42 and the hollow cylinder 40 is an enlarged ring 43 having a beveled shoulder 44 to seal against valve seat 24 of distal part 13. Hollow cylinder 40 functions identically to the elongate resilient member 20 in that the partially split and longitudinally open annular extension allows flow to pass to and across the beveled shoulder 44 when same is displaced from the valve seat 24.

A method of providing the catheter adapter 10 with an integral valve having the elongate resilient member 20 which allows the needle 18 to pass through the valve in a resealable manner includes the catheter adapter having a distal part and a proximal part which are designed to fit together and capture the elongate resilient member. The method has the steps of locating either of the parts 12 and 13 along an axis for placing the elongate resilient member 20 along the axis of the aligned part 12 or 13. Thereafter the step of placing the remaining part 12 or 13 along the axis and moving it along the axis toward the other part 12 or 13 to capture the resilient member 20 in a passage defined by the assembly of the parts 12 or 13.

Engaging the axially aligned parts 12 and 13 with each other and about the elongate resilient member 20 to axially compress the elongate resilient member 20 in the passage in which the resilient member 20 is captured is the next step. Forcing the elongate resilient member 20 against a valve seat 23 to seal transversely the passage and prevent flow therethrough is the valve forming step of the preferred method. Placing the needle 18 carried on the hub 17 along the axis "A" and through a septum like end 28 of the elongate resilient member 20 allows the needle 18 to be withdrawn from the septum like end 28 to thereafter reseal the passage 14.

The method step of engaging is provided by fitting the parts 12 and 13 and applying fastening means, e.g. glue, cement, RF welding, or mechanical means to secure in fluid tight manner the engagement between the parts 12 and 13. The elongate resilient member 20 is first placed along the axis "A" and within the distal part 12 before the proximal part 13 is applied to complete the catheter adapter 11 and compress the elongate resilient member 20 within the passage 14 formed therethrough.

FIG. 4 shows the valve 11 in the open position. The flow is from the luer fitting 22 through reliefs 45 in the collar 36. The collar 36 is rigid so that radial flow through the reliefs 45 may take place even though the elongate resilient member 20 is compressed by the fitting 22. The flow channels 37 include, in the preferred embodiment, longitudinal grooves 46 on the inside of the distal part 12 permitting the flow to easily pass through the annular space 33 between the elongate resilient member 20 and the distal part 12. The flow channels 37 terminate distally in exit ports 47 which provide support shoulders 48 therebetween to hold the septum like end 28 when the elongate member 20 is compressed. The support shoulders 48 keep the exit ports 47 patent allowing flow to pass from the flow channels 37 through the exit ports 47 and into the catheter 15. Should the flow direction be opposite that shown in Figure 4, the valve 11 will work the same way.

Figure 7:
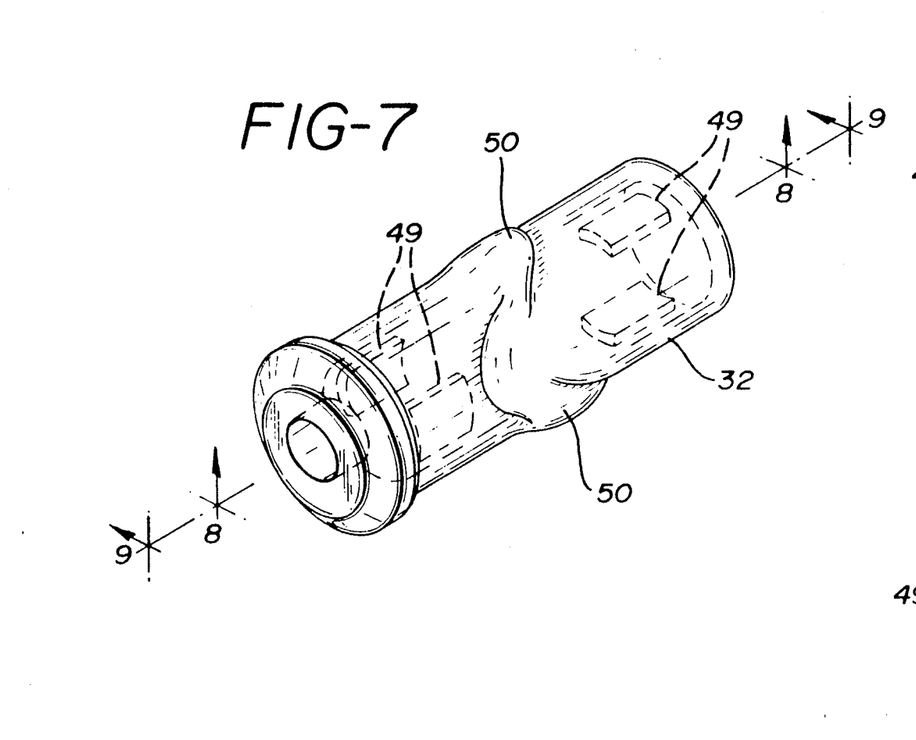
FIG. 7 is a perspective view of the elongate member shown folded or collapsed as it would be under axial loading.
Figure 8:
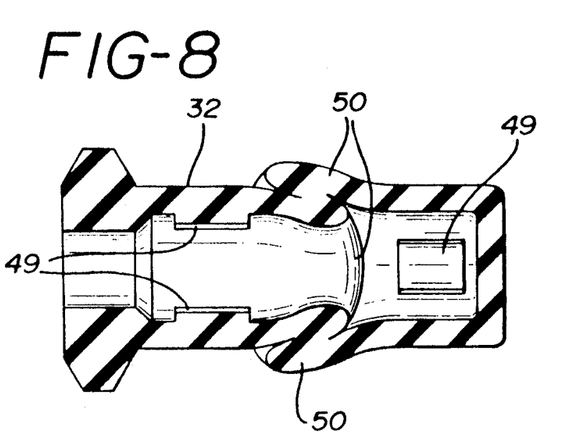
FIG. 8 is a view in cross section as would be seen along line 8—8 of FIG. 7.
Figure 9:
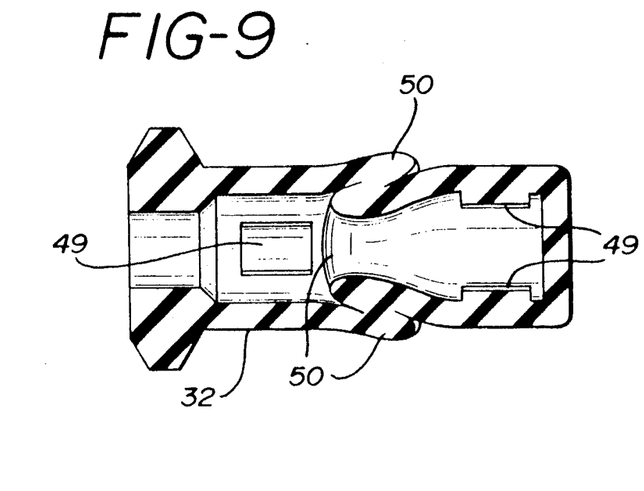
FIG. 9 is a view in cross section as would be seen along line 9—9 of FIG. 7.

The reduced cylindrical body 32 on the elongate resilient member 20 is designed to encourage the folding of the reduced cylindrical body 32 of the elongate resilient member 20 during compression such that the length reduction is sufficient to permit flow through the passage. The preferred design is arranged with ribs 49 placed longitudinally along the inside of the reduced cylindrical body 32 so that folding takes place in preferred directions. As illustrated in Figure 4 the reduced cylindrical body 32 is bowed under compression. It is preferred that the reduced cylindrical body 32 fold as shown in Figures 7, 8 and 9. The ribs 49 reinforce the reduced cylindrical body 32 and encourage the folding as shown so that transverse folds 50 are a direct result of the positioning of the ribs 49 across from and ninety degrees relative to one another. The transverse folds 50 are thus a result of the placement of ribs 49 and the compression.

The septum like end 28 is held in the distal part 12 in radial compression by an interference fit in the distal area 34. The slightly smaller size and similar shape of the distal area is selected to hold the septum like end 28 of the elongate resilient member 20 so that the radial compression thereacross assures that the resealable nature of the septum like end 28 is maintained after the needle 18 is removed.

What is claimed is:

1. An over the needle catheter with a needle and hub assembly and a catheter adapter having an integral valve comprising:
    a catheter adapter having a distal part and a proximal part joined together to form a passage therethrough along an axis thereof, the distal part connecting to a catheter tube for providing fluid communication therewith and through the passage;
    a valve assembly positioned within the passage about the axis and having an elongate resilient member captured within the passage and between the distal part and the proximal part for a compression fit therebetween to thereby normally prevent fluid communication through the passage;
    a proximal portion of the valve assembly provided to be engaged by a fluid dispenser fitting shaped to extend into the passage of the proximal part and axially compress the elongate resilient member when the fluid dispenser fitting is within the catheter adapter proximal part;
    a valve seat disposed within the passage and on the proximal part, the valve seat being formed as a generally frusto conical surface located coaxial about the axis and facing the distal part of the catheter adapter in position to engage a chamfered surface on the elongate resilient member to form a seal therebetween preventing fluid communication when the elongate resilient member is compressed between the distal part and the proximal part and allowing fluid communication when the seal is broken by axial compression of the elongate resilient member by the fluid dispenser fitting;
    a needle hub assembly having a hub which conjugates with the proximal part of the catheter adapter and a needle on the hub extending from the hub and through the passage when the hub is conjugated with the proximal part of the catheter adapter, and
    an internal cavity on the elongate resilient member extending axially and distally from the chamfered surface to a septum like end across the elongate resilient member for permitting the needle to pass through the septum like end in a resealable fashion upon placement and withdrawal of the needle therethrough.

2. The catheter adapter with an integral valve of claim 1 wherein the distal part and the proximal part each are provided with conjugating surfaces arranged to fit in mating engagement together forming the passage through the catheter adapter.

3. The catheter adapter with an integral valve of claim 1 wherein the elongate resilient member is molded of a material and has a flanged end for supporting the chamfered surface and a diametrically reduced cylindrical body extending to the septum like end and wherein an annular space is in the passage between the diametrically reduced cylindrical body and the distal part, the passage joins in a distal area of the catheter adapter.

4. The catheter adapter with an integral valve of claim 3 wherein the distal area includes flow channels which extend between the annular space and the distal part whereat the catheter tube joins in fluid communication the passage.

5. The catheter adapter with an integral valve of claim 3 wherein the diametrically reduced cylindrical body and its internal cavity therethrough act to provide a section of weakness permitting the elongate member to preferentially collapse under axial compression by the fluid dispenser fitting.

6. The catheter adapter with an integral valve of claim 5 wherein the diametrically reduced cylindrical body has at least a rib along the reduced cylindrical body to resist collapse and encourage folding where one or more the ribs are not located.

7. The catheter adapter with an integral valve of claim 5 wherein the distal area is shaped to receive the septum like end and hold the septum like end in radial compression to seal about the needle passing therethrough or after removal of the needle.

8. The catheter adapter with an integral valve of claim 1 wherein a proximal end of the internal cavity of the elongate resilient member conjugates with a collar disposed in axially alignment with and upon the open end thereof, the collar shaped to abut with the fluid dispenser fitting when extended into the distal part.

9. A method of providing an over the needle catheter assembly having a catheter adapter with an integral valve having an elongate resilient member which allows a needle to pass through the valve in a resealable manner, the catheter adapter having distal and proximal parts designed to fit together and capture the elongate resilient member, the method having the steps of:

locating either of the parts along an axis and placement of the elongate resilient member along the axis of the aligned part, placing the remaining part along the axis and then moving the remaining part along the axis toward the other part for capture of the resilient member in a passage defined by the assembly of the parts;

engaging the axially aligned parts with each other and about the elongate resilient member to axially compress and capture the elongate resilient member within the passage and thereby force the elongate resilient member against a valve seat for sealing transversely the passage and preventing flow therethrough, and placing a needle carried on a hub along the and through a septum like end of the elongate resilient member so that the needle may be withdrawn from the septum like end which thereafter reseals the passage.

10. The method of claim 9 wherein the step of engaging is provided by fitting the parts and applying fastening means to secure in fluid tight manner the engagement between the parts.

11. The method of claim 9 wherein the proximal part of the catheter adapter is aligned along the axis and the elongate resilient member is disposed along the axis within the proximal part before the distal part is applied along the axis to complete the catheter adapter and compress the elongate resilient member within the passage formed therethrough.

* * * * *